United States Patent [19]

Scharf

[11] 4,200,589

[45] Apr. 29, 1980

[54] PROCESS FOR PREPARING ACETONE FROM ISOBUTYRALDEHYDE

[75] Inventor: Helmut Scharf, Schermbeck, Fed. Rep. of Germany

[73] Assignee: Chemische Werke Hüls A.G., Marl, Fed. Rep. of Germany

[21] Appl. No.: 973,579

[22] Filed: Dec. 27, 1978

[30] Foreign Application Priority Data

Jan. 21, 1978 [DE] Fed. Rep. of Germany ....... 2802672

[51] Int. Cl.$^2$ .............................................. C07C 45/00
[52] U.S. Cl. ................................................. 260/593 R
[58] Field of Search ..................................... 260/593 R

[56] References Cited

U.S. PATENT DOCUMENTS

| | | | |
|---|---|---|---|
| 3,767,711 | 10/1973 | Gobron et al. ................... | 260/593 R |
| 3,855,304 | 12/1974 | Sakakibara et al. ............. | 260/593 R |
| 3,966,822 | 6/1976 | Fukui et al. ....................... | 260/593 R |
| 4,000,199 | 12/1976 | Obenaus et al. .................. | 260/593 R |

*Primary Examiner*—Norman Morgenstern
*Assistant Examiner*—James H. Reamer
*Attorney, Agent, or Firm*—Gilbert L. Wells

[57] ABSTRACT

This is an improvement in the process for preparing acetone by the catalytic, oxidative decarbonylation of isobutyraldehyde in the gaseous phase by passing a mixture consisting of isobutyraldehyde, oxygen and an inert diluent, when desired, at higher temperatures and at contact-times from 0.1 to 10 seconds over a carrier catalyst where the novel catalyst contains a mixture of copper oxide or manganese oxide, or a mixture thereof, with zinc oxide.

A mixture comprising about 1 to 4.5 vol. % of isobutyraldehyde, about 1.2 to 99 vol. % of oxygen and an inert diluent, when desired, is passed over a catalyst at a temperature of about 130° to 180° C., consisting of about 0.1 to 6% by weight of Cu or Mn, or a mixture thereof, in the form of their oxides and of about 1 to 10% by weight of Zn in the form of zinc oxide on aluminum oxide as the carrier.

8 Claims, No Drawings

PROCESS FOR PREPARING ACETONE FROM ISOBUTYRALDEHYDE

CROSS-REFERENCE TO RELATED APPLICATION

Applicant claims priority under 35 USC 119 for application Ser. No. P 28 02 672.4-42, filed Jan. 21, 1978 in the Patent Office of the Federal Republic of Germany.

BACKGROUND OF THE INVENTION

The present invention is concerned with a process for preparing acetone by catalytic oxidative decarbonylation of isobutyraldehyde in the gaseous phase, which evidences extraordinarily high selectivity at full conversion of isobutyraldehyde.

Isobutyraldehyde is obtained in large amounts as an inevitable by-product when propene is hydroformylated to n-butyraldehyde. The isobutyraldehyde by-product has failed to be applicable in any way to covering the costs necessary for the propene starting material and the hydroformylation process. There is a technical possibility of efficiently processing the isobutyraldehyde by catalytically oxidizing it to acetone. The two processes known are the liquid and the gaseous phase processes.

Higher yields and better selectivities are obtained when oxidizing in the gaseous phase as opposed to the liquid phase. In this process, gaseous isobutyraldehyde is passed together with molecular oxygen in the presence of an inert diluent over a carrier catalyst.

The state of the art of preparing acetone by the catalytic oxidative decarbonylation of isobutyraldehyde in the gaseous phase may be ascertained by reference to U.S. Pat. Nos. 3,804,902; 3,855,304 and 4,000,199, the disclosures of which are incorporated herein.

German Published application No. 21 57 307 and U.S. Pat. Nos. 3,804,902 and 3,855,304 disclose a catalyst of manganese oxide on activated aluminum oxide. While such a catalyst offers high yields, the selectivities on the other hand are relatively slight. Better selectivities are obtained using copper oxide on activated aluminum oxide or zinc oxide, as disclosed in U.S. Pat. No. 4,000,199. This process too suffers from the drawback that a still appreciable proportion of the isobutyraldehyde is burned to carbon dioxide. Thus, under the most favorable conditions, using copper oxide on aluminum oxide, a selectivity of 93 mol % is obtained, i.e., from 6 to 7 mol % of isobutyraldehyde are burned to carbon dioxide and water. When copper oxide on zinc oxide is used, a selectivity of 96 mol % is in fact obtained, but the yield on the other hand is only 90.5%. The economy of such a process of the present invention, however, demands high yield and high selectivity, because basically valuable propene, which is contained in the isobutyraldehyde, is burned to useless carbon dioxide and water in the total combustion of the isobutyraldehyde. In addition, about fivefold the amount of the heat released per mole of isobutyraldehyde in the oxidative decarbonylation of the isobutyraldehyde to acetone is released in the total combustion. Even when there is only 6 mol % of total combustion, the ratio of the amounts of heat of total to partial combustion is about 1:3. These additional large amounts of heat magnify the problem of heat transfer and entail a lower throughput over the catalyst, whereby again the economy of the process is decreased.

SUMMARY OF THE INVENTION

Having in mind the limitations of the prior art, it is an object of the present invention to further improve these methods with respect to yield and selectivity.

In the prior art methods acetone is prepared by the catalytic, oxidative decarbonylation of isobutyraldehyde in the gaseous phase by passing a mixture consisting of isobutyraldehyde, oxygen and an inert diluent, when desired, at higher temperatures and at contact-times from about 0.1 to 10 seconds over a carrier catalyst containing copper oxide or manganese oxide.

The object of the present invention is achieved by operating the prior art methods under the following critical conditions:

(a) the mixture of isobutyraldehyde and oxygen has about 1 to 4.5 volume percent of isobutyraldehyde and about 1.2 to 99 volume percent of oxygen;

(b) the temperature of reaction is about 130° to 180° C.; and, (c) the catalyst, on an aluminum oxide carrier, is about 0.1 to 6% by weight copper or manganese, or a mixture thereof, in their oxide forms and about 1 to 10% by weight zinc as zinc oxide.

The content in copper or manganese of the finished catalyst is between about 0.1 and 6% by weight, and that of zinc between 1 and 10% by weight. The metals are present in the finished catalyst in the form of oxides. Aluminum oxide is used as the carrier. Higher proportions of copper, manganese or zinc are possible, though they no longer induce further improvements. Preferably, the proportion of copper or manganese is between 1 and 3% by weight and that of zinc between 2 and 5% by weight.

The concentration of the isobutyraldehyde in the gas mixture may vary between about 1 and 4.5% by volume. Higher and lower concentrations are permissible, however, the lesser concentrations are economically insignificant and heat transfer becomes a problem at higher concentrations where tolerable space-time yields are assumed.

The oxygen concentration of the input gas depends on the isobutyraldehyde concentration. The lowest molar ratio of isobutyraldehyde to oxygen should be 1:1.2. If the ratio is less, the yield for constant or even slightly increased selectivity drops rapidly. Molar ratios of isobutyraldehyde to oxygen from 1:2 to 1:3 are preferred. The isobutyraldehyde to oxygen ratio however, may exceed those values. Thus, the reaction may also be carried out with pure oxygen provided the isobutyraldehyde concentration is selected to be moderate enough (about 1 to 2.5% by volume). Using pure oxygen, however, is appropriate only when the carbon monoxide in the exhaust gases is burned to carbon dioxide, the carbon dioxide so obtained being removed with the carbon dioxide generated as a side product in the formation of acetone by means of pressurized washing from the exhaust flow, and the residual oxygen fed back to the reaction. As a rule, an inert diluent is added to the input gas. Suitable diluents for instance are the following: nitrogen, steam, carbon dioxide or carbon monoxide. Preferred diluents are nitrogen and/or steam, the nitrogen being obtained when air is used as a preferred oxidizer. Using pure steam allows operating with oxygen as a circulating gas. The required amounts of diluents are unambiguously obtained from the concentrations of isobutyraldehyde and of oxygen, but generally vary from 0 to 97.8 volume percent.

The temperature of reaction is between about 130° and 180° C. Selectivity drops markedly above 180° C., and yield falls off strongly below 130° C. Preferably, the inside reactor temperature is between 140° and 160° C. The reactors are externally cooled. Cooling and temperature-maintaining means are the conventional ones used in industry. A boiler tube reactor is advantageously used for good heat transfer.

The dwell time of the input materials in the catalyst bed (contact time) depends on the composition of the input mixture and on the temperature of reaction and varies within a range from about 0.1 to 10 seconds. Preferably, contact time is between 1 and 4 seconds. The conversion ordinarily is carried out at standard pressure or slightly above up to 5 bars, though it may also be implemented at higher ones. The pressure is limited upwards by the incipient formation of condensates, that is, by the occurrence of a liquid phase.

The catalysts used can be prepared by, as disclosed in U.S. Pat. Nos. 3,804,902; 3,855,304 and 4,000,199, impregnation of commercial, activated aluminum oxide and zinc and copper salt solutions or zinc and manganese salt solutions with ensuing drying and calcining of the products.

The deposition of the metal compounds on the carrier can be implemented in one single step by using solutions containing both types of metal ions, or in two steps, by first depositing one metal compound on the carrier, drying the product and calcining it, and then the other, with the same steps being used. It is furthermore possible to deposit all three metal oxides, namely zinc oxide, copper oxide and manganese oxide together on an aluminum carrier, however, such a combination offers no additional advantages with respect to the dual combination of zinc-oxide/copper-oxide on aluminum oxide or zinc-oxide/manganese oxide on aluminum oxide.

The advantages which can be obtained using the process of the invention most of all consist in that isobutyraldehyde is approximately quantitatively converted at full yield into acetone. The by-products created in the process now occur only as traces, and there is only an extremely minute or no total combustion of the isobutyraldehyde to carbon dioxide and water, whereby the heat to be transferred is significantly reduced.

The present invention is illustrated in the following specific Examples 1-10, and data from these examples is tabulated in the table which follows, along with data from comparison tests taken from Example 2 of German Published Application 21 57 307 and Example 5 of U.S. Pat. No. 4,000,199.

EXAMPLES 1-10

112 g of activated aluminum oxide (strands, 4 mm in diameter, 4 mm long, from catalyst supplier Houdry-Huels) were impregnated with 98 cm$^3$ of an aqueous solution containing 20.5 g of $Zn(NO_3)_2.6H_2O$, then dried for 16 hours at 110° C. and calcined for 16 hours at 350° C. Thereupon, the calcined catalyst was impregnated with 98 cm$^3$ of an aqueous copper tetramine carbonate solution containing 14.1% of copper ions and again was dried for 16 hours at 110° C. and calcined for 16 hours at 350° C. The finished catalyst contained 2.3% by weight of copper and 2.3% by weight of zinc in the form of their oxides.

60 cm$^3$ of the catalyst so prepared were placed into a steel reaction tube with an inner diameter of 20 mm and kept at constant temperature by boiling water, the reaction temperature was 160° C., the contact time was 2 seconds, and the inside pressure of the reactor was 1.5 bars. The catalyst was subjected to a gaseous mixture consisting of 2.5 vol. % of isobutyraldehyde, 45.5 vol. % of air and 52.0 vol. % of steam. The gaseous mixture leaving the reactor was tested by gas-chromatography.

Further catalysts were prepared according to the description above, but with different contents in metals, and used at different temperatures.

Again, a catalyst was prepared and tested, for which the sequence of carrier coating with the metal oxides was reversed (Example 8). As regards Example 9, pure oxygen was used instead of air as the oxidizer.

The results are listed in the following table:

| EXAMPLE | Catalyst Composition [%] | Reaction Temperature [°C.] | Conversion of Isobutyraldehyde [%] | Selectivity with Respect to Acetone or to Conversion of Isobutyraldehyde [Mol %] | Remarks |
| --- | --- | --- | --- | --- | --- |
| 1 | Cu 2.3; Zn 2.3 | 160 | 100.0 | 98.5 | |
| 2 | Cu 2.3; Zn 2.3 | 156 | 99.6 | 99.9 | |
| 3 | Cu 2.3; Zn 2.3 | 144 | 100.0 | 99.0 | |
| 4 | Cu 2.3; Zn 2.3 | 136 | 99.0 | 98.2 | |
| 5 | Cu 1.7; Zn 3.7 | 148 | 99.6 | 99.6 | |
| 6 | Cu 1.8; Zn 6.4 | 142 | 99.3 | 98.4 | |
| 7 | Mn 1.0; Zn 4.4 | 164 | 99.2 | 98.5 | |
| 8 | Zn 2.3; Cu 2.3 | 152 | 99.4 | 99.1 | |
| 9 | Cu 2.3; Zn 2.3 | 144 | 99.9 | 99.0 | |
| 10 | Mn 1.0; Cu 1.3; Zn 2.3 | 156 | 99.6 | 99.9 | |
| Comparison | Mn 25 | 250 | 93.0 | 85 | German Published Application 21 57 307 Example 2 |
| Comparison | Cu 3.4 | 270 | 99.1 | 93.0 | U.S. Pat. No. 4,000,199 Example 5 |

I claim:

1. In a process for the preparation of acetone by the catalytic oxidative decarbonylation of isobutyraldehyde in the gaseous phase, wherein a gaseous mixture comprising isobutyraldehyde and oxygen is contacted with a metal oxide catalyst containing copper oxide or manganese oxide for contact times of about 0.1 to 10 seconds, the improvement comprising:

said gaseous mixture comprising about 1 to 4.5 vol. % of isobutyraldehyde and about 1.2 to 99 vol. % of oxygen, said process is conducted at a temperature of about 130° to 180° C., and said metal oxide catalyst consists of about 0.1 to 6% by weight of Cu, Mn, or a mixture thereof, in the form of their oxides and of about 1 to 10% by weight of Zn in the form of zinc oxide on aluminum oxide as a carrier.

2. The process of claim 1, wherein said metal oxide catalyst consists of about 1 to 3% by weight of said Cu, Mn or mixtures thereof, and of about 2 to 5% by weight of Zn.

3. The process of claim 1, wherein said process is conducted at a temperature of about 140° to 160° C.

4. The process of claim 1, wherein said gaseous mixture comprises an inert diluent selected from the group consisting of nitrogen, steam or a mixture thereof.

5. The process of claim 1, wherein said contact times are about 1 to 4 seconds.

6. The process of claim 2, wherein said metal oxide catalyst consists of about 1 to 3% by weight of Cu and about 2 to 5% by weight of Zn.

7. The process of claim 2, wherein said metal oxide catalyst consists of about 1 to 3% by weight of Mn and about 2 to 5% by weight of Zn.

8. The process of claim 2, wherein said metal oxide catalyst consists of about 1 to 3% by weight of a mixture of Mn and Cu and about 2 to 5% by weight of Zn.

* * * * *